US011261072B2

(12) United States Patent
Takaku et al.

(10) Patent No.: US 11,261,072 B2
(45) Date of Patent: Mar. 1, 2022

(54) ASEPTIC FILLING MACHINE AND ASEPTIC FILLING METHOD

(71) Applicant: Dai Nippon Printing Co., Ltd., Tokyo (JP)

(72) Inventors: Hitoshi Takaku, Tokyo (JP); Atsushi Hayakawa, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 249 days.

(21) Appl. No.: 16/335,875

(22) PCT Filed: Sep. 22, 2017

(86) PCT No.: PCT/JP2017/034372
§ 371 (c)(1),
(2) Date: Mar. 22, 2019

(87) PCT Pub. No.: WO2018/056411
PCT Pub. Date: Mar. 29, 2018

(65) Prior Publication Data

US 2019/0256336 A1 Aug. 22, 2019

(30) Foreign Application Priority Data

Sep. 26, 2016 (JP) ............................. JP2016-187426
Oct. 21, 2016 (JP) ............................. JP2016-206501

(51) Int. Cl.
*B67C 7/00* (2006.01)
*B65B 55/10* (2006.01)
(Continued)

(52) U.S. Cl.
CPC ............ *B67C 7/0073* (2013.01); *A61L 2/186* (2013.01); *A61L 2/208* (2013.01); *B65B 55/04* (2013.01);
(Continued)

(58) Field of Classification Search
CPC .............. B67C 3/242; B67C 2003/227; B67C 2003/228; B67C 7/00; B67C 7/002;
(Continued)

(56) References Cited

U.S. PATENT DOCUMENTS 3,809,768 A 5/1974 Berry
4,987,726 A * 1/1991 Petho et al. .......... B67C 7/0073 53/425

(Continued)

FOREIGN PATENT DOCUMENTS

DE 198 17 735 C1 11/1999
EP 2 407 417 A1 1/2012

(Continued)

OTHER PUBLICATIONS

Extended European Search Report (Application No. 17853179.4) dated Apr. 23, 2020.

(Continued)

*Primary Examiner* — Stephen F. Gerrity
(74) *Attorney, Agent, or Firm* — Burr & Brown, PLLC

(57) ABSTRACT

An aseptic filling machine and an aseptic filling method are provided with which a petaloid-shape bottle or an unstable bottle is filled with sterilized content and sealed with a sterilized cap in an aseptic atmosphere is discharged without a delay from an aseptic zone to a non-aseptic zone and even if the petaloid-shape bottle or the unstable bottle falls over on a discharging conveyor when being discharged from the aseptic zone to the non-aseptic zone, a stopping time of the aseptic filling machine is shortened by providing a barrier chamber into which air containing a gas of a sterilizer is supplied and a discharge portion chamber that shields discharge portions that are provided downstream of the sealing portion that fills the content into the bottle and seals the bottle with the cap.

14 Claims, 12 Drawing Sheets

(51) Int. Cl.

| | |
|---|---|
| ***B65B 55/04*** | (2006.01) |
| ***B65B 63/00*** | (2006.01) |
| ***A61L 2/18*** | (2006.01) |
| ***A61L 2/20*** | (2006.01) |
| ***B65C 3/08*** | (2006.01) |
| *B67C 3/26* | (2006.01) |

(52) U.S. Cl.
CPC ............ *B65B 55/10* (2013.01); *B65B 63/005* (2013.01); *B65C 3/08* (2013.01); *B67C 7/002* (2013.01); *B67C 7/0053* (2013.01); *A61L 2202/23* (2013.01); *B67C 2003/2694* (2013.01)

(58) Field of Classification Search
CPC ..... B67C 7/004; B67C 7/0046; B67C 7/0053; B67C 7/0073; B67C 3/2642; B65B 55/027; B65B 55/025; B65B 55/02; B65B 55/04; B65B 55/10
USPC .................................. 53/282, 425, 426, 471
See application file for complete search history.

(56) References Cited

U.S. PATENT DOCUMENTS

| | | | | |
|---|---|---|---|---|
| 6,457,299 | B1 | 10/2002 | Schwenke et al. | |
| 6,786,249 | B2 * | 9/2004 | Armbruster et al. | A61L 2/208 141/105 |
| 2002/0083682 | A1 * | 7/2002 | Edwards et al. | B67C 7/0073 53/426 |
| 2009/0013645 | A1 * | 1/2009 | Mastio | B67C 7/0073 53/425 |
| 2010/0043915 | A1 * | 2/2010 | Sangi et al. | B65B 55/027 141/11 |
| 2010/0170867 | A1 | 7/2010 | Hayakawa | |
| 2011/0094616 | A1 | 4/2011 | Hayakawa et al. | |
| 2014/0260099 | A1 | 9/2014 | Braum et al. | |
| 2016/0263269 | A1 | 9/2016 | Hayakawa et al. | |

FOREIGN PATENT DOCUMENTS

| | | | | | |
|---|---|---|---|---|---|
| EP | 2 594 499 | A1 | | 5/2013 | |
| EP | 2 778 114 | A2 | | 9/2014 | |
| FR | 2 818 615 | A1 | | 6/2002 | |
| JP | H11-047242 | A1 | | 2/1999 | |
| JP | H11-079385 | A1 | | 3/1999 | |
| JP | 2003-146427 | A1 | | 5/2003 | |
| JP | 2010-189023 | A1 | | 9/2010 | |
| JP | 2014-051304 | A1 | | 3/2014 | |
| JP | 2015-116814 | A1 | | 6/2015 | |
| JP | 2015116814 | A | * | 6/2015 | B67C 7/0073 |
| JP | 2015-120555 | A1 | | 7/2015 | |
| JP | 2016-141400 | A1 | | 8/2016 | |
| JP | 2016-153316 | A1 | | 8/2016 | |

OTHER PUBLICATIONS

International Search Report and Written Opinion (Application No. PCT/JP2017/034372) dated Nov. 21, 2017.

* cited by examiner

SUPPLYING PREFORM

HEATING PREFORM

BLOW MOLDING

TAKING OUT BOTTLE

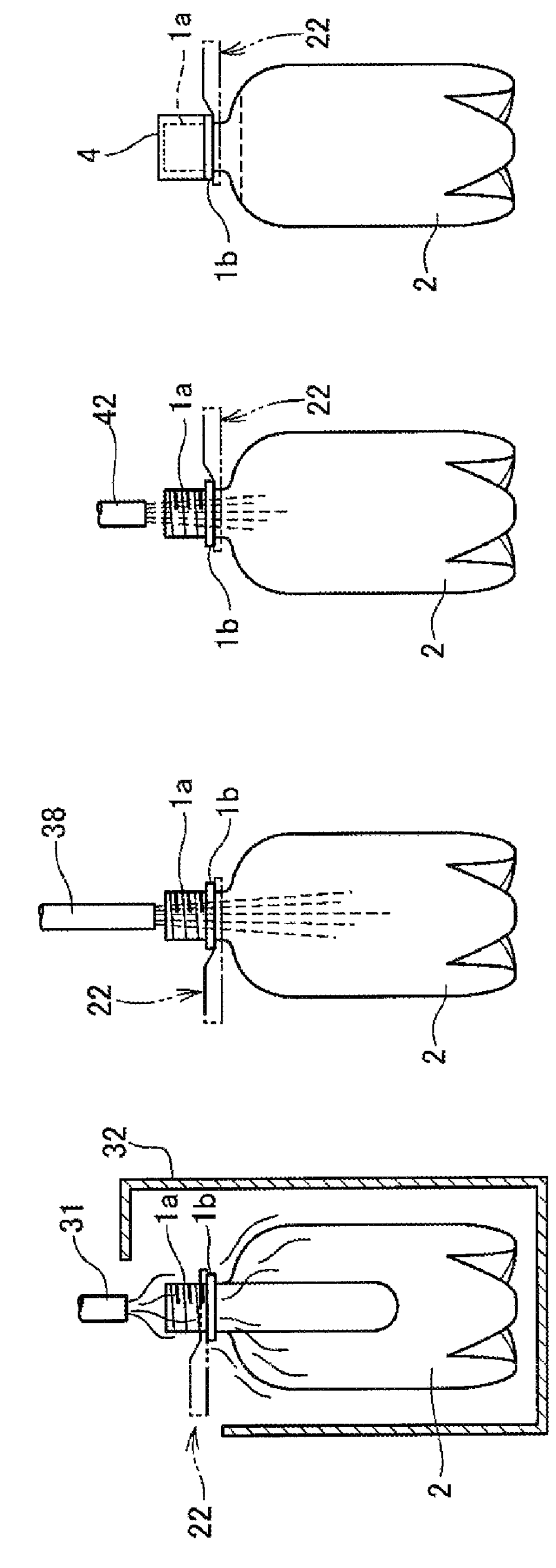
FIG. 5A BLASTING STERILIZER GAS
FIG. 5B AIR RINSING
FIG. 5C FILLING CONTENT
FIG. 5D SEALING

BLASTING STERILIZER GAS

BLASTING AIR

ASEPTIC FILLING MACHINE AND ASEPTIC FILLING METHOD

TECHNICAL FIELD

The present invention relates to an aseptic filling machine and an aseptic filling method in which a zone that supplies sterilizer-containing air is provided between an aseptic zone and a non-aseptic zone in order to discharge a product obtained by filling a drink or the like into a bottle and sealing the bottle in an aseptic atmosphere from the aseptic zone to the non-aseptic zone. The present invention also relates to an aseptic filling machine and an aseptic filling method in which, in order to discharge a product from an aseptic zone to a non-aseptic zone, a chamber is provided that discharges the product to the aseptic zone.

BACKGROUND ART

An apparatus for sterilizing containers has already been proposed in which, while a preform is being caused to continuously travel, the preform is introduced into a heating furnace, heated within the heating furnace to a temperature for molding a container, a gaseous matter is then blown into the heated preform to mold the preform into a bottle, and the bottle is then sterilized, filled with sterilized content, and sealed with a sterilized cap (Patent Literature 1). In this kind of apparatus, in an aseptic zone the sealed bottle is released from a state in which the bottle is conveyed by being suspended in midair by a gripper that grips a support ring of the bottle, and is discharged from the aseptic zone to a non-aseptic zone by a conveyor.

An apparatus for sterilizing containers has also been proposed that sterilizes a preform, fills sterilized content into a molded bottle, and seals the bottle with a sterilized cap (Patent Literature 2). In this case also, in an aseptic zone the sealed bottle is released from a state in which the bottle is conveyed by being suspended in midair by a gripper that grips a support ring of the bottle, and is discharged from the aseptic zone to a non-aseptic zone by a conveyor.

In an aseptic filling machine, in an aseptic zone a gripper releases its grip on a support ring of a sealed bottle to thereby place the sealed bottle on a conveyor. The conveyor on which the sealed bottle is placed is a first conveyor which travels in a circulating manner through the aseptic zone, and in addition to the first conveyor, a second conveyor which travels in a circulating manner through the non-aseptic zone, and an intermediate conveyor that travels in a manner in which the intermediate conveyor overlaps with an end portion of the first conveyor and an end portion of the second conveyor are also provided. Discharging a sealed bottle into a non-aseptic zone by causing the sealed bottle to travel on these conveyors has been proposed (Patent Literature 3). In this case, the intermediate conveyor travels in a circulating manner through the aseptic zone and the non-aseptic zone, and is continuously sterilized by being immersed in the liquid of a pool of sterilizer so as not to bring bacteria and the like from the non-aseptic zone into the aseptic zone.

Further, an apparatus has also been proposed that, instead of using an intermediate conveyor, transfers sealed bottles to a conveyor provided in a non-aseptic zone by means of a conveying apparatus that grips a support ring of the bottle, which is provided in an aseptic zone (Patent Literature 4). In this case, a shielding plate that separates the aseptic zone and the non-aseptic zone is provided diagonally at an angle from an upper part to a lower part, and the area of an opening portion is large.

CITATION LIST

Patent Literature

Patent Literature 1: Japanese Patent Laid-Open No. 2010-189023

Patent Literature 2: Japanese Patent Laid-Open No. 2015-116814

Patent Literature 3: Japanese Patent Laid-Open No. 11-79385

Patent Literature 4: Japanese Patent Laid-Open No. 2003-146427

SUMMARY OF INVENTION

Technical Problem

The available types of aseptic filling machines for bottles include a type in which a preform is supplied and molded into a bottle, after which the bottle is sterilized, and content is filled into the bottle and the bottle is then sealed in an aseptic atmosphere, and a type in which a preform is supplied, the preform is sterilized, and then, in an aseptic atmosphere, content is filled into and sealed in a bottle obtained by molding the sterilized preform. In each of these two types of aseptic filling machines, after filling, a sterilized cap must be screwed onto a mouth portion of the bottle and sealed, and the thus-obtained bottle must be discharged from the aseptic zone to a non-aseptic zone. An opening portion is provided in the aseptic zone in order to discharge the bottle. However, if bacteria or the like enters from the opening portion, the aseptic condition of the aseptic zone can no longer be maintained. Therefore, the aseptic zone is kept at a positive pressure with aseptic air, thereby maintaining the aseptic condition of the aseptic zone.

The infiltration of bacteria and the like into the aseptic zone through air can be prevented by keeping the aseptic zone at a positive pressure. However, the infiltration of bacteria and the like that adheres to a discharging apparatus for the bottles cannot be prevented by keeping the aseptic zone at a positive pressure. The method disclosed in Patent Literature 4 uses a grip conveyor when discharging bottles, and when the speed is accelerated the bottles sometimes fall over when the bottles are released from the grip conveyor. Further, because a slope is provided at the opening portion, the area of the opening portion increases and it is difficult to maintain the aseptic condition by means of a positive pressure.

Therefore, the method disclosed in Patent Literature 3 is being adopted. However, in order to cause an end portion of the first conveyor in the aseptic zone to overlap and combine with an end portion of the intermediate conveyor that is provided so as to overlap between the aseptic zone and the non-aseptic zone, no conveyor chain for conveying bottles is provided at a central portion of the first conveyor, and the width of a conveyor chain of the intermediate conveyor is narrow. Therefore, although a problem does not arise when conveying bottles that have a normal shape, in the case of bottles which have a carbonated drink as the content thereof, the bottles may sometimes fall over in the aseptic zone. The base of a bottle that has a carbonated drink as the content thereof is a petaloid shape, and in a case where the protruding portion of the petaloid shape does not ride onto the end portion of the first conveyor, or in a case where the protruding portion of the petaloid shape exceeds the width of the intermediate conveyor, sometimes the bottle leans over and falls. In addition, a method also exists that, by changing the lengths of conveyor chains constituting the conveyors and connecting the conveyor chains, moves bottles from a first conveyor that is in an aseptic zone to an intermediate conveyor without causing an end portion of the first conveyor and an end portion of the intermediate conveyor to overlap. However, according to this method also, in some cases a petaloid protrusion of a bottle becomes caught in a gap between connecting sections of the conveyor chains, and the bottle falls over in the aseptic zone. If a bottle falls over in the aseptic zone, it is difficult to remove the bottle by performing an operation from outside while the aseptic filling machine continues operating. In this case, it is necessary to stop operation of the aseptic filling machine and remove the fallen bottle. When such an operation is performed, the aseptic condition of the aseptic zone is lost. Thereafter, sterilization of the aseptic zone must be performed once more in order to resume operation of the aseptic filling machine. As a result, the aseptic filling machine must be stopped for a long time period, and the business person suffers an inhibition to production. Furthermore, even if a bottle has a normal shape, in some cases a similar inconvenience occurs when a bottle which has a small ground contact area falls over or a bottle that has a high center of gravity and which is liable to totter falls over.

The present invention has been made to solve the problems described above, and an object of the present invention is to provide an aseptic filling machine and an aseptic filling method with which a petaloid-shaped bottle or an unstable bottle into which sterilized content was filled and which was sealed with a sterilized cap in an aseptic atmosphere can be discharged from the aseptic zone to a non-aseptic zone without being caused to fall over. A further object of the present invention is to provide an aseptic filling machine and an aseptic filling method with which, even when a petaloid-shaped bottle or an unstable bottle into which sterilized content was filled and which was sealed with a sterilized cap in an aseptic atmosphere falls over on a conveyor when being discharged from the aseptic zone to a non-aseptic zone, the stopping time of the aseptic filling machine can be shortened.

Solution to Problem

An aseptic filling machine according to the present invention is an aseptic filling machine for bottles that includes at least a sterilizing portion, a filling portion and a sealing portion, wherein a barrier chamber including a supply apparatus for air containing a sterilizer is provided downstream of the sealing portion.

Further, in the aseptic filling machine according to the present invention, it is favorable to provide an outlet chamber including an exhaust apparatus downstream of the barrier chamber.

Further, in the aseptic filling machine according to the present invention, it is favorable for a conveying apparatus to be provided which grips or supports a mouth portion of the bottle and conveys the bottle from the sealing portion to the barrier chamber and the outlet chamber.

Further, in the aseptic filling machine according to the present invention, it is favorable for a conveyor to be provided which conveys the bottle that is inside the outlet chamber to outside of the aseptic filling machine.

Further, in the aseptic filling machine according to the present invention, it is favorable for a label attaching apparatus to be provided which attaches a label to the bottle inside the outlet chamber.

Further, in the aseptic filling machine according to the present invention, it is favorable for the sterilizer to contain hydrogen peroxide.

Further, in the aseptic filling machine according to the present invention, it is favorable for an exhaust air mixing apparatus to be provided for mixing air that is exhausted from the sterilizing portion with the air containing a sterilizer.

An aseptic filling machine according to the present invention is an aseptic filling machine for bottles that includes at least a sterilizing portion, a filling portion and a sealing portion, wherein a discharge portion chamber that shields a discharge portion including a discharging apparatus that discharges bottles after sealing from an aseptic zone to a non-aseptic zone is provided downstream of the sealing portion.

Further, in the aseptic filling machine according to the present invention, it is favorable for the discharging apparatus to include a discharging conveyor that circulates at least from the aseptic zone to the non-aseptic zone, and to include a sterilizer tank in which the discharging conveyor is immersed in a sterilizer.

Further, in the aseptic filling machine according to the present invention, it is favorable for a discharge portion chamber sterilization apparatus that sterilizes inside of the discharge portion chamber to be provided in the discharge portion chamber, and for the discharge portion chamber sterilization apparatus to include at least a sterilizer spraying nozzle that sprays sterilizer into the discharge portion chamber.

Further, in the aseptic filling machine according to the present invention, it is favorable for the discharge portion chamber to include an aseptic air supplying apparatus that supplies aseptic air into the discharge portion chamber.

An aseptic filling method according to the present invention includes at least a sterilization step of sterilizing a preform or a bottle, a filling step of filling sterilized content into the bottle in an aseptic atmosphere, and a sealing step of sealing the bottle in which the content is filled with a sterilized cap in an aseptic atmosphere, wherein, after the sealing step, the bottle that is sealed is conveyed to a barrier chamber to which air containing a sterilizer is supplied.

Further, in the aseptic filling method according to the present invention, it is favorable for the bottle that is conveyed to the barrier chamber to be conveyed to an outlet chamber that includes an exhaust apparatus.

Further, in the aseptic filling method according to the present invention, it is favorable to grip or support a mouth portion of the bottle and convey the bottle to the barrier chamber and the outlet chamber.

Further, in the aseptic filling method according to the present invention, it is favorable for the bottle to be discharged to outside of an aseptic filling machine by a conveyor that is provided within the outlet chamber.

Further, in the aseptic filling method according to the present invention, it is favorable to attach a label to the bottle after the bottle is conveyed to the outlet chamber.

Further, in the aseptic filling method according to the present invention, it is favorable for the sterilizer to contain hydrogen peroxide.

Further, in the aseptic filling method according to the present invention, it is favorable to mix air that is exhausted in the sterilization step with the air containing a sterilizer.

An aseptic filling method according to the present invention includes at least a sterilization step of sterilizing a preform or a bottle, a filling step of filling sterilized content into the bottle in an aseptic atmosphere, and a sealing step of sealing the bottle in which the content is filled with a sterilized cap in an aseptic atmosphere, wherein, after the sealing step, the bottle that is sealed is conveyed inside a discharge portion chamber that is shielded and maintained in an aseptic atmosphere, and is discharged from the discharge portion chamber to a non-aseptic zone.

Further, in the aseptic filling method according to the present invention, it is favorable for the bottle to be discharged from the discharge portion chamber to the non-aseptic zone by conveying the bottle by means of a discharging conveyor that circulates through inside of the discharge portion chamber and the non-aseptic zone, and for the conveyor to be immersed in a sterilizer.

Further, in the aseptic filling method according to the present invention, it is favorable to sterilize the inside of the discharge portion chamber by sequentially spraying a sterilizer, water and aseptic heated air into the inside of the discharge portion chamber.

Further, in the aseptic filling method according to the present invention, it is favorable to maintain the inside of the discharge portion chamber in an aseptic atmosphere by supplying aseptic air into the inside of the discharge portion chamber.

SUMMARY OF INVENTION

According to the aseptic filling machine and the aseptic filling method of the present invention, even if the base of a bottle that is filled with sterilized content and sealed with a sterilized cap in an aseptic atmosphere is a petaloid shape or the bottle is an unstable shape, the bottle is discharged from the aseptic atmosphere to a non-aseptic atmosphere without falling over. Further, even if a bottle falls over in an aseptic zone when the bottle is being discharged due to the base of the bottle being a petaloid shape or the bottle having an unstable shape, the stopping time of the aseptic filling machine can be shortened.

BRIEF DESCRIPTION OF DRAWINGS

FIGS. 4A-4D are views illustrating steps performed by a molding portion of the aseptic filling machine according to the embodiment of the present invention, in which FIG. 4A illustrates a preform supplying step, FIG. 4B illustrates a preform heating step, FIG. 4C illustrates a blow molding step, and FIG. 4D illustrates a bottle extracting step.

FIGS. 5A-5D are views illustrating steps performed by a sterilizing portion and a filling portion of the aseptic filling machine according to the embodiment of the present invention, in which FIG. 5A illustrates a sterilizer gas spraying step, FIG. 5B illustrates an air-rinsing step, FIG. 5C illustrates a filling step, and FIG. 5D illustrates a sealing step.

FIGS. 10A and 10B are views illustrating steps performed by a preform sterilizing portion of the aseptic filling machine according to the embodiment of the present invention, in which FIG. 10A illustrates a sterilizer gas spraying step of spraying a sterilizer gas at a preform, and FIG. 10B illustrates an air blowing step of blowing air at a preform.

DETAILED DESCRIPTION OF THE INVENTION

In the following, first and second forms for implementing the present invention will be described with reference to the drawings.

First Embodiment

Firstly, an outline of an aseptic filling machine composed of a molding portion, a sterilizing portion, a filling portion, a barrier chamber and an outlet chamber will be described starting from the supply of a preform by way of FIG. 1, and the details of each portion will be described by way of FIGS. 4A-4D, FIGS. 5A-5D, FIG. 6, FIG. 7, FIG. 8 and FIG. 9. According to the first embodiment, even in a case where the base of a bottle is a petaloid shape or a case where a bottle has an unstable shape, the bottle is discharged at a high speed from an aseptic zone to a non-aseptic zone without falling over. Further, the aseptic zone is not contaminated by infiltration of bacteria or the like.

(Outline of Aseptic Filling Machine and Aseptic Filling Method)

Figure 1:
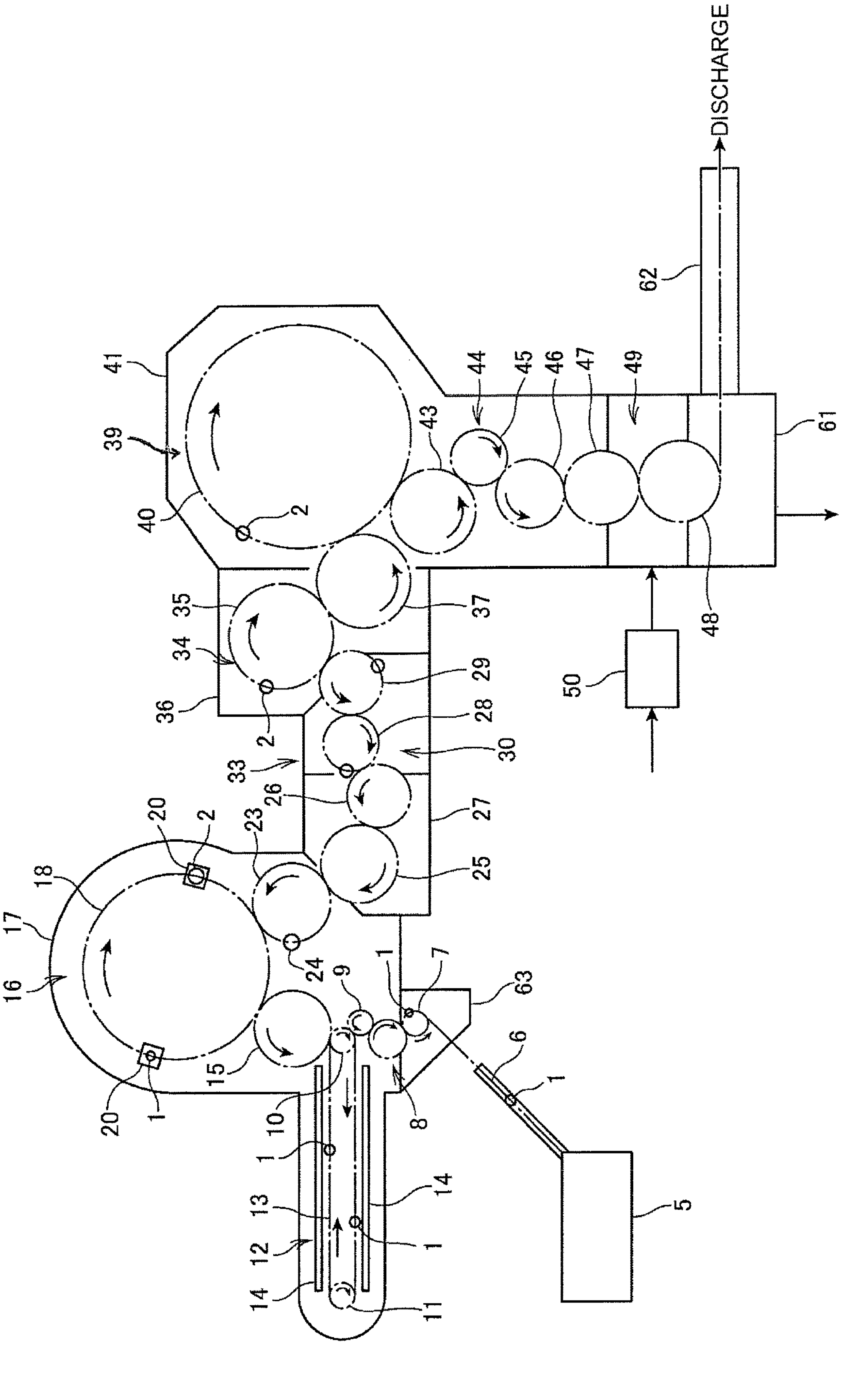
FIG. 1 is a plan view illustrating an outline of one example of an aseptic filling machine according to a first embodiment of the present invention.

As illustrated in FIG. 1, the aseptic filling machine according to the first embodiment includes: a preform supplying apparatus 5 that supplies a preform 1; a molding portion 16 that molds the preform 1 into a bottle 2; a sterilizing portion 30 that sterilizes the bottle 2 that was molded; an air-rinsing portion 34 that performs air-rinsing of the sterilized bottle 2; and a filling portion 39 that fills sterilized content into the bottle 2 that was subjected to air-rinsing and seals the bottle 2 with a sterilized cap 4. In addition, the aseptic filling machine includes a barrier chamber 49 through which the sealed bottle 2 passes and to which air containing a sterilizer is supplied, and an outlet chamber 61 in which the bottle 2 is placed on a discharging conveyor 62 and discharged into a non-aseptic zone.

The molding portion 16 is shielded by a molding portion chamber 17, the sterilizing portion 30 is shielded by a sterilizing portion chamber 33, the air-rinsing portion 34 is shielded by an air-rinsing portion chamber 36, and the filling portion 39 and a sealing portion 44 are shielded by a filling portion chamber 41. An atmosphere shut-off chamber 27 is provided between the molding portion 16 and the sterilizing portion 30 to ensure that gas or mist of a sterilizer that is generated at the sterilizing portion 30 does not flow into the molding portion 16. The atmosphere shut-off chamber is exhausted, and therefore the gas or mist of a sterilizer generated at the sterilizing portion 30 does not flow into the molding portion 16.

Aseptic air that was sterilized by an aseptic filter is supplied to the sterilizing portion chamber 33, the air-rinsing portion chamber 36 and the filling portion chamber 41, and the interior of each of these chambers is maintained at a positive pressure. The pressure that is maintained at a positive pressure is set so as to be highest in the filling portion chamber 41, and to be progressively lower toward the upstream side, with the pressure being lower in the air-rinsing portion chamber 36 than in the filling portion chamber 41, and further lower in the sterilizing portion chamber 33. The pressure inside the atmosphere shut-off chamber 27 is maintained at approximately the same pressure as the atmospheric pressure by exhaust of air.

Air containing a sterilizer is supplied to the barrier chamber 49, and the pressure inside the barrier chamber 49 is made lower than in the filling portion chamber 41 to ensure that the air containing a sterilizer does not flow into the filling portion chamber 41. In addition, the outlet chamber 61 is exhausted so that sterilizer contained in the air that is supplied to the barrier chamber does not leak to outside, and the pressure inside the outlet chamber 61 is maintained at approximately the same pressure as the atmospheric pressure or at a pressure that is equal to or less than the atmospheric pressure.

(Detailed Description of Aseptic Filling Machine and Aseptic Filling Method)

Figures 4A, 4B, 4C, 4D:
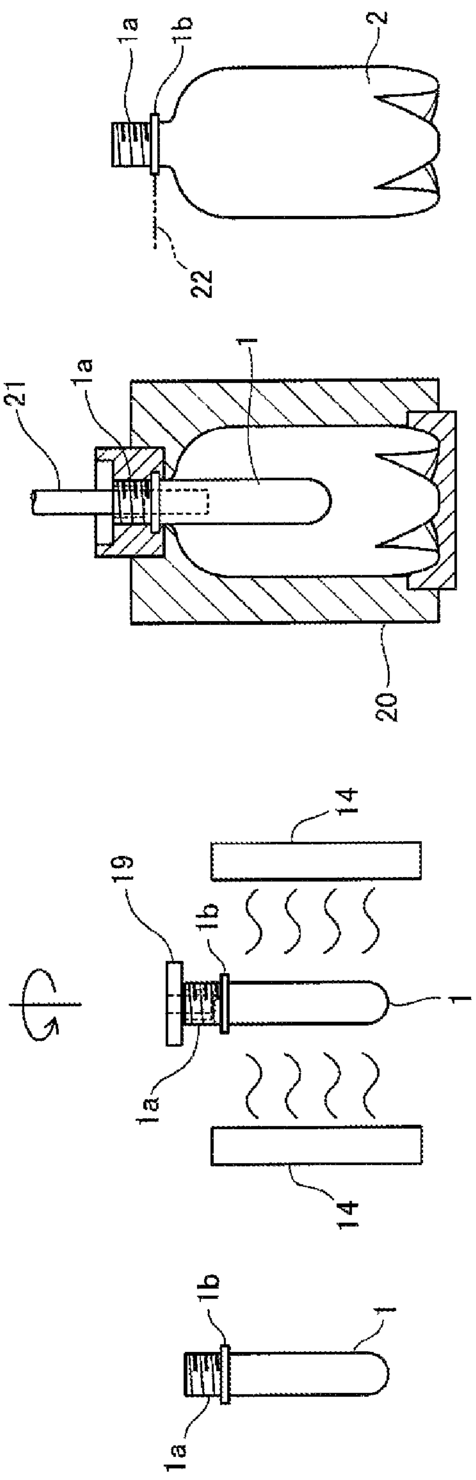

First, the preforms 1 illustrated in FIG. 4A are conveyed from the preform supplying apparatus 5 shown in FIG. 1 to the molding portion 16 consecutively at a desired speed by a preform conveyance conveyor 6.

The preform 1 in the first embodiment is a bottomed cylindrical body having a test tube shape. The preform 1 is formed with a mouth portion 1*a* like that of the bottle 2 shown in FIG. 4D when performing initial molding thereof. A male thread is formed at the mouth portion 1*a* concurrently with molding of the preform 1. Further, a support ring 1*b* for conveying is formed below the mouth portion 1*a* in the preform 1. The preform 1 or the bottle 2 is gripped by a gripper 22 through the support ring 1*b*, and travels through the inside of the aseptic filling machine. The preform 1 is molded by injection molding, compression molding or the like. The material of the preform 1 is composed of a thermoplastic resin such as polyethylene terephthalate, polyethylene naphthalate, polypropylene or polyethylene, and may be a resin simple substance or a mixture of these thermoplastic resins, and may include recycled thermoplastic resin. Further, to impart a barrier property, a thermoplastic resin such as an ethylene-vinyl alcohol-copolymer or polyamide having an aromatic amine such as a metaxylylene diamine as a monomer may be included as a layer or as a mixture.

The preform 1 that was supplied to the molding portion 16 is conveyed by wheels 7 and 8 on which a large number of the grippers 22 are provided at regular intervals, and thus reaches a heating furnace conveying wheel 9. At such time, as shown in FIG. 4B, the preform 1 is released from the gripper 22, and a spindle 19 is inserted into the mouth portion 1*a* of the preform 1, and the preform 1 is conveyed to a heating furnace 12.

As illustrated in FIG. 4B, the preform 1 that entered the heating furnace 12 is heated to a temperature suitable for subsequent blow molding, by an infrared heater 14 or other heating device. A suitable temperature is within the range of 90 to 130° C.

Note that, the temperature of the mouth portion 1*a* of the preform 1 is suppressed to a temperature of not more than 70° C. to prevent deformation and the like.

Further, as illustrated in FIG. 4B, the spindle 19 is inserted into the mouth portion 1*a* of the preform 1, and the preform 1 is conveyed through the inside of the heating furnace 12 while rotating. A plurality of the spindles 19 are provided at fixed intervals on an endless chain 13. The endless chain 13 rotates by means of pulleys 10 and 11. It is also possible to convey the preform 1 while rotating in an inverted state by inserting a mandrel in place of the spindle 19 into the preform 1.

The heated preform 1 is released from the spindle 19 and gripped by the gripper 22, and is conveyed to a mold wheel 18 of a blow molding machine via a wheel 15. As illustrated in FIG. 4C, the heated preform 1 is blow-molded into the bottle 2 by means of a mold 20 provided on the mold wheel 18. The mold 20 and a blow nozzle 21 are arranged at a plurality of places around the mold wheel 18, and swivel at a constant speed around the mold wheel 18 together with the rotation of the mold wheel 18. When the heated preform 1 arrives, the mold 20 clamps the preform 1. Next, the blow nozzle 21 is paired with the preform 1, an extension rod (not shown) is guided to a hole provided in the blow nozzle 21, inserted into the preform 1, and gaseous matter such as air is then blown into the preform 1 from the blow nozzle 21, and thus the bottle 2 is molded within the mold 20. As illustrated in FIG. 4D, the molded bottle 2 is taken out from the mold 20, and the support ring 1*b* is gripped by the gripper 22 provided on an inspection wheel 23 to thereby transfer the molded bottle 2 to the inspection wheel 23.

Figure 2:
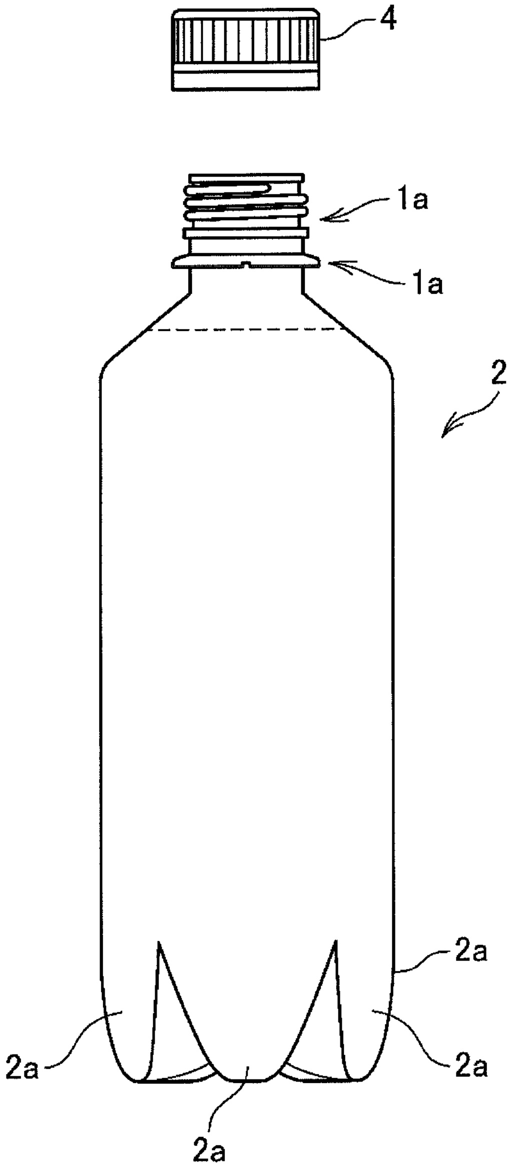
FIG. 2 is a side view illustrating an example of the bottle shape of a product produced by the aseptic filling machine according to the embodiment of the present invention.
Figure 3:
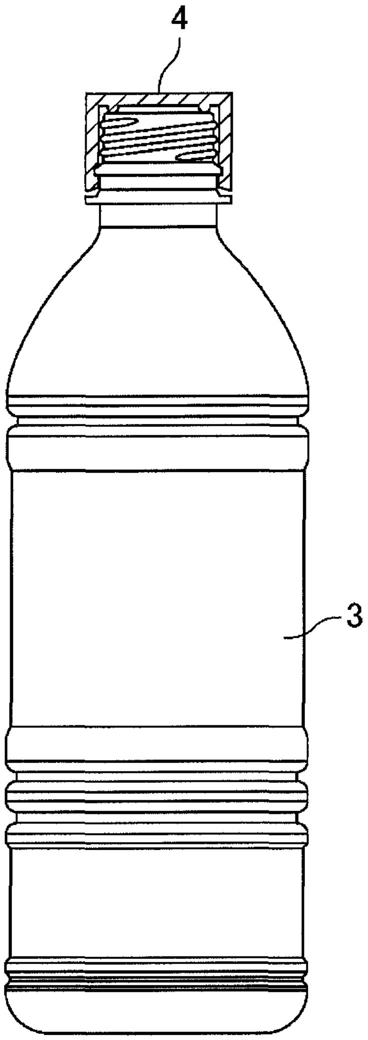
FIG. 3 is a side view illustrating a modification of the bottle shape of a product produced by the aseptic filling machine according to the embodiment of the present invention.

The bottle 2 that is molded by the aseptic filling machine according to the first embodiment of the present invention has a petaloid-shaped base as illustrated in FIG. 2. When a carbonated drink is filled in a bottle such as a bottle 3 having a substantially flat base as illustrated in FIG. 3, the base may sometimes bulge in a convex shape due to an increase in the internal pressure directly after filling. Therefore, when filling a carbonated drink, the bottle 2 having a petaloid shape that has petaloid legs 2*a* at the base thereof as illustrated in FIG. 2 is used. The number of petaloid legs 2*a* is usually set arbitrarily within the range of 5 to 9. The depth of a valley portion of each petaloid leg 2*a* is also arbitrarily set. A bottle that is molded by the aseptic filling machine according to the embodiment of the present invention may also have a shape like the commonly used bottle 3 that has a substantially flat base that is illustrated in FIG. 3. In particular, the aseptic filling machine according to the present invention is suitable for a bottle that is unstable even though the base thereof is flat.

The molded bottle 2 is subjected to an inspection by an inspection machine 24 provided at the periphery of the inspection wheel 23 to thereby detect the bottle temperature and inspect the bottle body portion, the support ring, the top surface of the bottle mouth portion, the bottle base and the like. If the inspection machine 24 determines that there is an abnormality, the molded bottle 2 is discharged to outside of the aseptic filling machine by an unshown discharging apparatus.

Detection of the bottle temperature is performed by detecting the surface temperature of the bottle 2 to determine the suitability of the bottle 2. The temperature sensor is, for example, an infrared thermometer, and it is also possible to use another kind of thermometer. It is necessary that residual heat from the time when the bottle was molded remains in the bottle 2 in order to properly sterilize the bottle 2, and it is desirable that the temperature detected by the temperature sensor is 50° C. or more.

Further, the bottle body portion, the support ring, the top surface of the bottle mouth portion and the bottle base are photographed by a camera, and the state of each of these locations is examined. The photographed images are processed by an image processing apparatus to determine the presence/absence of abnormalities such as flaws, contaminants, deformation and discoloring. If an abnormality of the bottle 2 exceeds an allowable range, the bottle 2 is determined to be abnormal.

The bottles 2 which are not determined to be abnormal in the inspection by the inspection machine 24 are conveyed to the sterilizing portion 30 via wheels 25 and 26 in the atmosphere shut-off chamber 27 which is provided between the molding portion 16 and the sterilizing portion 30 to ensure that gas or mist of sterilizer that arises in the sterilizing portion 30 does not flow into the molding portion 16.

The bottle 2 that was conveyed to the sterilizing portion 30 is sterilized at a wheel 28. A sterilizer gas spraying step is illustrated in FIG. 5A. A sterilizer gas spraying nozzle 31 is provided for spraying sterilizer gas at the bottle 2. The sterilizer gas spraying nozzle 31 is fixed so that a nozzle hole in the tip thereof can directly face the opening of the mouth portion 1*a* of the bottle 2 that travels directly below the sterilizer gas spraying nozzle 31. Further, as necessary, as illustrated in FIG. 5A, a sterilizer gas spraying tunnel 32 is provided along the travelling path of the bottle 2 below the sterilizer gas spraying nozzle 31. One sterilizer gas spraying nozzle 31 or a plurality of the sterilizer gas spraying nozzles 31 may be provided. The gas of a sterilizer that is sprayed at the bottle 2 flows into the interior of the bottle 2 and sterilizes the inner surface of the bottle 2. At this time, because the bottle 2 travels through the inside of the sterilizer gas spraying tunnel 32, gas or mist of the sterilizer also flows along the outer surface of the bottle 2 and sterilizes the outer surface of the bottle 2.

Figure 6:
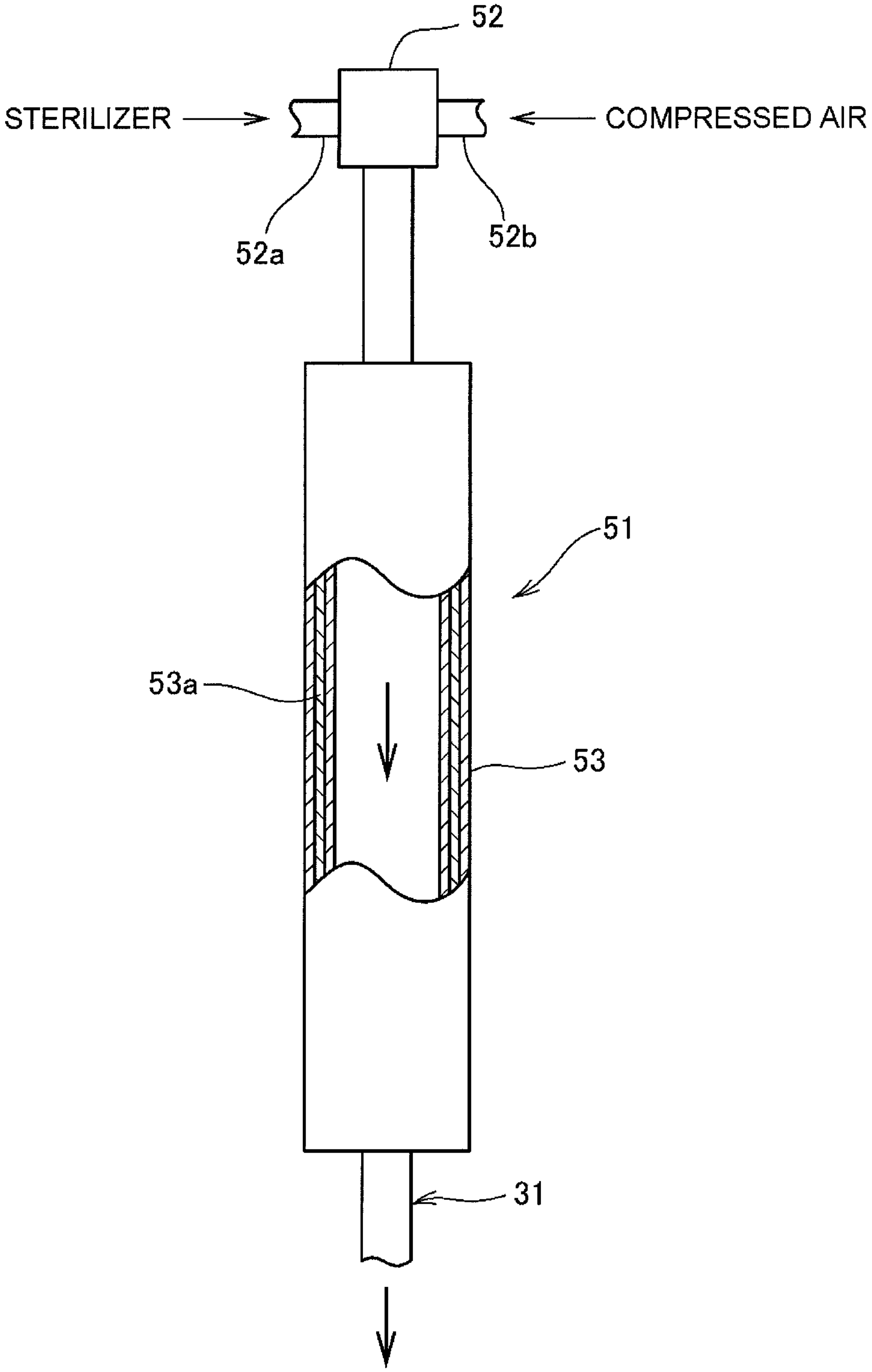
FIG. 6 illustrates a sterilizer gas generator that is incorporated into the aseptic filling machine according to the embodiment of the present invention.

The gas or mist of the sterilizer is, as illustrated in FIG. 6, sterilizer that is gasified by a sterilizer gas generator 51 or is mist that is formed when gasified sterilizer condenses. The sterilizer gas generator 51 includes a sterilizer supply portion 52 that is a twin-fluid spray nozzle that supplies a sterilizer in the form of drops, and a vaporizing portion 53 that vaporizes the sterilizer that is supplied from the sterilizer supply portion 52 by heating the sterilizer to a temperature equal to or lower than the decomposition temperature thereof. The sterilizer supply portion 52 is configured to receive the sterilizer and compressed air that are introduced from a sterilizer supply path 52*a* and a compressed air supply path 52*b*, respectively, and to spray the sterilizer into the vaporizing portion 53. The vaporizing portion 53 is a pipe that incorporates a heater 53*a* disposed between inner and outer walls thereof, and heats and vaporizes the sterilizer sprayed into the pipe. The gas of the vaporized sterilizer is ejected to the outside of the vaporizing portion 53 from the sterilizer gas spraying nozzle 31. A configuration may also be adopted in which the vaporizing portion 53 is heated by dielectric heating instead of the heater 53*a*.

As the operating condition of the sterilizer supply portion 52, for example, the pressure of the compressed air is adjusted within the range of 0.05 Mpa to 0.6 Mpa. Further, the sterilizer may fall by gravity or pressure may be applied thereto, and the amount supplied can be freely set. For example, the sterilizer is supplied in an amount within a range of 1 g/min to 100 g/min. Furthermore, sprayed sterilizer is vaporized by heating the inner surface of the vaporizing portion 53 within a range from 140° C. to 450° C.

The gas of the sterilizer that is ejected is sprayed from the sterilizer gas spraying nozzle 31 into the bottle 2 as illustrated in FIG. 5A. Although the spray amount of the gas or mist of the sterilizer is arbitrarily set, the spray amount is determined by the amount of sterilizer supplied to the sterilizer gas generator 51 and the spray time period. A plurality of the sterilizer gas generators 51 may be provided. The spray amount also varies depending on the size of the bottle 2.

The sterilizer preferably contains at least hydrogen peroxide. An appropriate range of the content thereof is from 0.5% by mass to 65% by mass. If the content is lower than 0.5% by mass, the sterilizing power may be insufficient in some cases, while if the content is higher than 65% by mass, the sterilizer will be difficult to handle from the viewpoint of safety. A further preferable range is from 0.5% by mass to 40% by mass. When the content is equal to or lower than 40% by mass, it is easier to handle the sterilizer, and the residual amount of sterilizer after sterilization can be reduced since the concentration is low.

When a hydrogen peroxide solution is adopted as the sterilizer, the spray amount of gas of the hydrogen peroxide solution is as follows. The amount of hydrogen peroxide adhering to the inner surface of the bottle 2 that is produced by the gas of the hydrogen peroxide solution that is sprayed at the inner surface of the bottle 2 from the sterilizer gas spraying nozzle 31 is preferably within a range of 30 μL/bottle to 150 μL/bottle as the amount of a hydrogen peroxide solution containing 35% by mass of hydrogen peroxide, and more preferably is within a range of 50 μL/bottle to 100 μL/bottle. Further, the hydrogen peroxide concentration of the gas of the hydrogen peroxide solution that is sprayed into the bottle 2 is preferably within a range of 2 mg/L to 20 mg/L, and more preferably is within a range of 5 mg/L to 10 mg/L.

Although the sterilizer contains water, the sterilizer may contain one or more of alcohols such as methyl alcohol, ethyl alcohol, isopropyl alcohol, n-propyl alcohol and butyl alcohol, ketones such as acetone, methyl ethyl ketone and acetylacetone, and glycol ether and the like.

The sterilizer may further contain an additive agent such as a compound having a sterilizing effect such as peracetic acid, acetic acid, a chlorine compound or ozone; a cationic surface active agent, a non-ionic surface active agent and a phosphate compound.

As illustrated in FIG. 1, the bottle 2 that was sterilized at the sterilizing portion 30 is conveyed via a wheel 29 to the air-rinsing portion 34. At an air-rinsing wheel 35 illustrated in FIG. 1, aseptic air is blown into the bottle 2 by an air-rinsing nozzle 38 as illustrated in FIG. 5B. The aseptic air may be at ordinary temperature, but is preferably heated. The aseptic air ejects sterilizer remaining inside the bottle 2, and decomposes the remaining sterilizer to further enhance the sterilizing effect, and thus also has an effect of eliminating contaminants in a case where contaminants remain inside the bottle 2.

A configuration may also be adopted in which the air-rinsing nozzle 38 is capable of performing vertical motion, and blows aseptic air inside the bottle 2. Further, a configuration may be adopted in which aseptic water, and not aseptic air, is introduced into the inside of the bottle 2 to rinse the inside of the bottle 2. A configuration may also be adopted in which aseptic air and aseptic water are used in combination to rinse the bottle 2.

The bottle 2 that was subjected to air-rinsing at the air-rinsing portion 34 is conveyed to the filling portion 39 via a wheel 37 as illustrated in FIG. 1. In the filling portion 39, at a wheel 40 illustrated in FIG. 1, content is filled into the bottle 2 by a filling nozzle 42 in the manner shown by a filling step illustrated in FIG. 5C. The content is sterilized beforehand. A predetermined amount of the content such as a drink is filled into the bottle 2 by the filling nozzle 42 that travels in synchronization with the bottle 2.

The bottle 2 into which content was filled is conveyed to the sealing portion 44 via a wheel 43 illustrated in FIG. 1. At a sealing wheel 45 provided in the sealing portion 44, in the manner shown in a sealing step illustrated in FIG. 5D, a cap 4 that was sterilized in advance is screwed onto the mouth portion 1*a* of the bottle 2 by an unshown capper which is provided in the sealing wheel 45, to thereby seal the bottle 2.

The sealed bottle 2 is released from the gripped state by the gripper 22 of the sealing wheel 45, and is conveyed onto the circumference of a wheel 46 by unshown body-portion pot guides which are provided in a large number at the outer circumference of the wheel 46. The wheel 46 illustrated in FIG. 1 is a conveying apparatus in which the body-portion pot guides are provided at fixed intervals at the periphery thereof. The sealed bottle 2 is transferred via the wheel 46 to a wheel 47 that is a conveying apparatus in which body-portion pot guides are provided, and is thereby conveyed to the barrier chamber 49. The barrier chamber 49 includes an apparatus for supplying sterilizer-containing air 50 that is illustrated in FIG. 7, and air containing a sterilizer is supplied into the inside of the barrier chamber 49.

Figure 7:
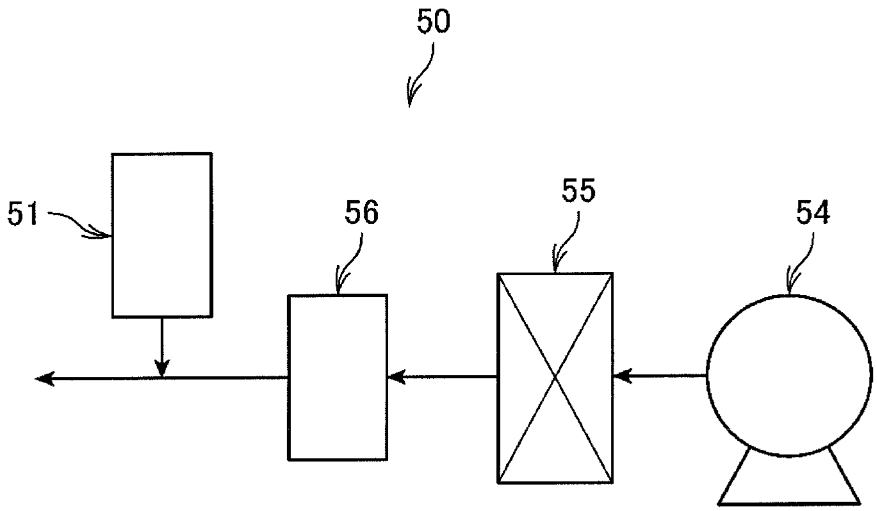
FIG. 7 illustrates an apparatus for supplying sterilizer-containing air that is incorporated into the aseptic filling machine according to the first embodiment of the present invention.

As illustrated in FIG. 7, the apparatus for supplying sterilizer-containing air 50 is composed of a blower 54, an aseptic filter 55 for sterilizing air blown by the blower 54, a heating apparatus 56 that, as required, further heats the aseptic air, and a sterilizer gas generator 51 that supplies sterilizer to aseptic air.

The sterilizer gas generator 51 is the same kind of apparatus as the sterilizer gas generator 51 that is used for sterilization of the bottle 2. Further, the same kind of sterilizer is used, and the sterilizer preferably contains at least hydrogen peroxide, and an appropriate range of the content thereof is from 0.5% by mass to 65% by mass. If the content is lower than 0.5% by mass, the sterilizing power may be insufficient in some cases, while if the content is higher than 65% by mass, the sterilizer will be difficult to handle from the viewpoint of safety. A further preferable range is from 0.5% by mass to 40% by mass. When the content is equal to or lower than 40% by mass, it is easier to handle the sterilizer.

The air containing a sterilizer is preferably heated by the heating apparatus 56. In a case where the concentration of the sterilizer is high or a case where the liquid temperature of the content to be filled is low, in some cases components of the sterilizer may condense on the surface of the bottle 2, and this can be prevented by such heating. A preferable range of the temperature of the air containing a sterilizer is from 40 to 70° C. If the temperature is lower than 40° C., components of the sterilizer cannot be prevented from condensing on the surface of the bottle 2, and if the temperature is higher than 70° C., the bottle 2 may deform.

The gas of the sterilizer that is introduced into the apparatus for supplying sterilizer-containing air 50 from the sterilizer gas spraying nozzle 31 is diluted with aseptic air, and is thereafter supplied to the barrier chamber 49. In a case where the sterilizer contained in the air that is supplied to the barrier chamber 49 is a hydrogen peroxide solution, an appropriate range of the concentration of the hydrogen peroxide in the gas is from 0.1 mg/L to 10 mg/L. If the concentration is less than 0.1 mg/L, it will not be sufficient for preserving the sterility of the inside of the barrier chamber 49, while if the concentration is more than 10 mg/L, it will be excessive for maintaining the aseptic condition of the barrier chamber.

Although the barrier chamber 49 is kept at a positive pressure, the internal pressure in the barrier chamber 49 is set to a lower pressure than in the filling portion chamber 41 which is kept at a positive pressure by aseptic air. For example, in a case where the internal pressure of the filling portion chamber 41 is in the range of 20 Pa to 40 Pa, the internal pressure of the barrier chamber 49 is set, for example, within the range of −30 Pa to 30 Pa, which is a lower pressure than inside the filling portion chamber 41. Preferably, the internal pressure of the barrier chamber 49 is set within the range of 0 Pa to 30 Pa.

Figure 8:
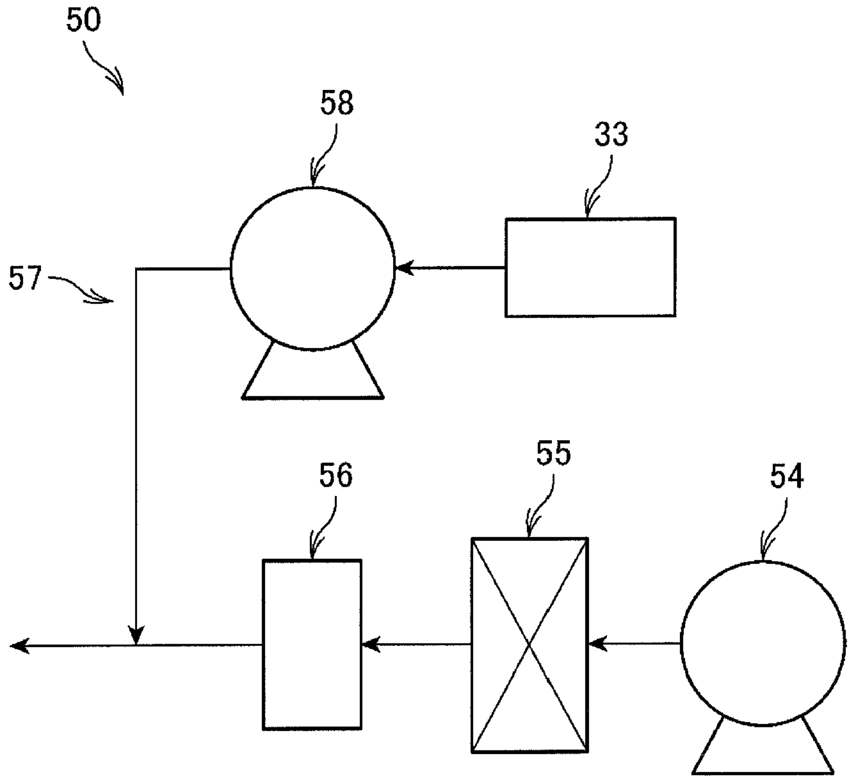
FIG. 8 illustrates a discharged air mixing apparatus that is incorporated into the aseptic filling machine according to the first embodiment of the present invention.

As the gas of the sterilizer that is supplied to the barrier chamber 49, gas of the sterilizer that is contained in air exhausted from the sterilizing portion chamber 33 may be used, and not the gas of the sterilizer generated by the sterilizer gas generator 51. As illustrated in FIG. 8, an exhaust gas mixing apparatus 57 that mixes exhaust gas from the sterilizing portion chamber 33 and aseptic air by means of an exhaust gas blower 58 may be provided in the apparatus for supplying sterilizer-containing air 50 shown in FIG. 7. Although in this case the exhaust gas of the sterilizing portion chamber 33 is used, exhaust gas of a sterilizing portion for the cap 4, not shown in the drawings, may be used. In addition, in a case where sterilization of the preform 1 is performed, exhaust gas of a preform sterilizing portion may be used. Further, a configuration may be adopted in which these exhaust gases and gas of the sterilizer generated by the sterilizer gas generator 51 are combined and supplied as air containing a sterilizer to the barrier chamber 49.

The sealed bottle 2 is conveyed to the outlet chamber 61 by a wheel 48 in which body-portion pot guides are provided. The outlet chamber 61 includes an exhaust apparatus, and exhausts gas or mist of the sterilizer that flows in from the barrier chamber 49 to outside of the aseptic filling machine. Although not shown in the drawings, the exhaust apparatus includes a blower for exhausting gas or the like, and an apparatus that detoxifies or collects the sterilizer before exhausting gas or the like to outside of the aseptic filling machine. Because the outlet chamber 61 is exhausted, the pressure therein is approximately 0 Pa or equal to or lower than 0 Pa.

The bottle 2 that was conveyed to the outlet chamber 61 is placed on the discharging conveyor 62 from a body-portion pot guide of the wheel 48, and is then discharged to outside of the aseptic filling machine. The outlet chamber 61 is a non-aseptic zone, and even if the bottle 2 falls over on the discharging conveyor 62 inside the outlet chamber 61, a worker can lift up the bottle 2. Therefore, there is no hindrance to production if the bottle 2 falls over on the discharging conveyor 62.

Figure 9:
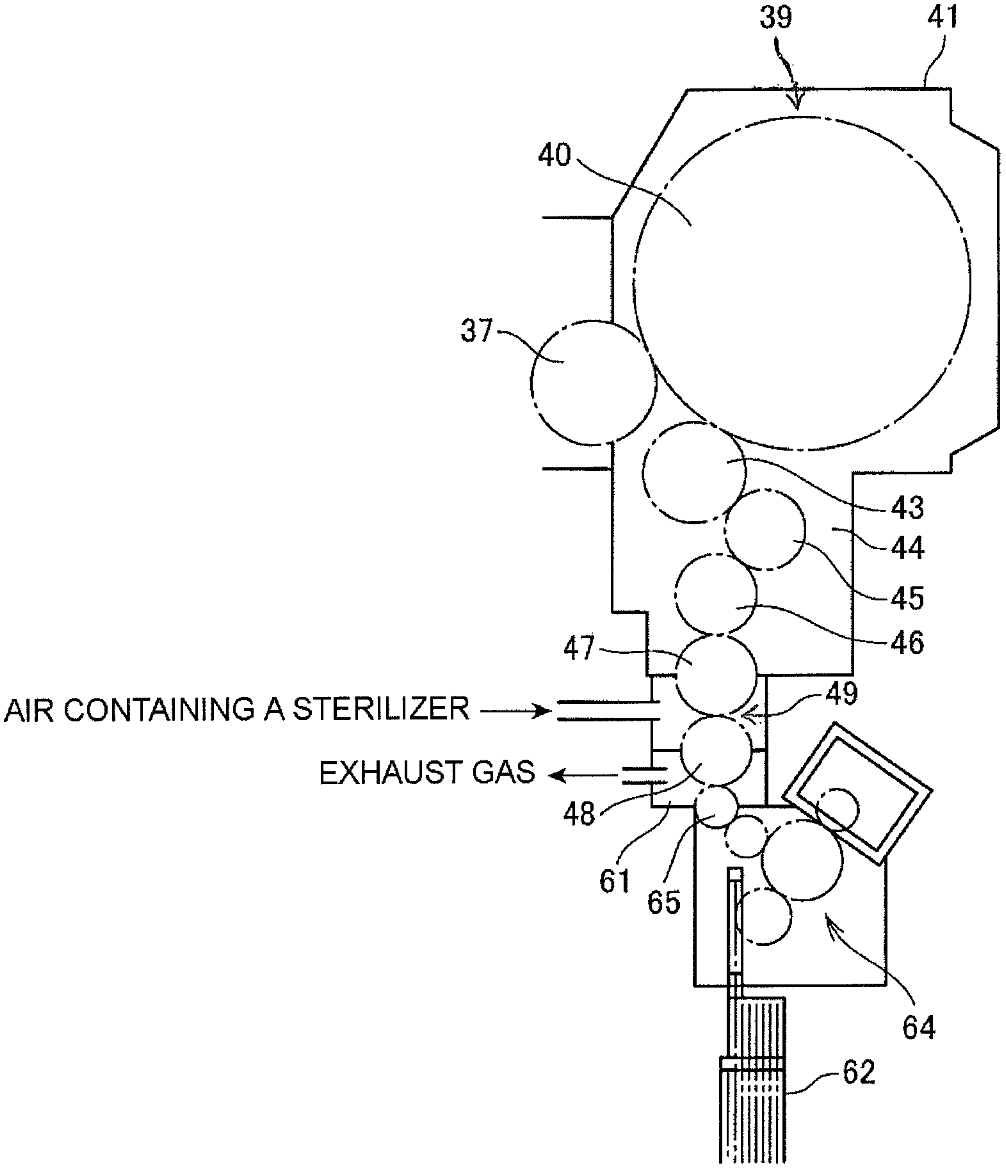
FIG. 9 is a plan view illustrating an outline of one part of the aseptic filling machine having a label attaching apparatus according to the first embodiment of the present invention.

As illustrated in FIG. 9, a label attaching apparatus 64 can also be provided downstream of the outlet chamber 61. The bottle 2 is transferred to the label attaching apparatus 64 by a wheel 65 provided in the outlet chamber 61. A label is attached to the bottle 2 by the label attaching apparatus 64. The label may be or any shape or form, such as a wrap label, a cylindrical shrink label or a shrink wrap label. The bottle 2 to which the label is attached is discharged to outside of the aseptic filling machine by the discharging conveyor 62, and as necessary, the label may be caused to shrink by heating the bottle 2 from the outside.

By linking the label attaching apparatus 64 to the outlet chamber 61, it is not necessary to align the bottles 2 when transferring the bottles 2 to the label attaching apparatus 64, and thus the apparatus can be simplified and the productivity can be improved. In other words, a conveying apparatus for conveying the bottles 2 from the outlet chamber 61 to the label attaching apparatus 64, and an aligning apparatus for transferring the bottles 2 to the label attaching apparatus 64 are unnecessary. Furthermore, as a result, time is not required in order to convey and align the bottles 2.

The first embodiment of the present invention has been described in detail based on FIG. 1 and the like. The aseptic filling machine according to the first embodiment that is described above sterilizes the bottle 2 that is obtained by molding the preform 1. However, aseptic filling machine may also be a machine that sterilizes the preform 1. Hereunder, an aseptic filling machine including a sterilizing portion that sterilizes preforms is described as another embodiment.

Figure 10A:
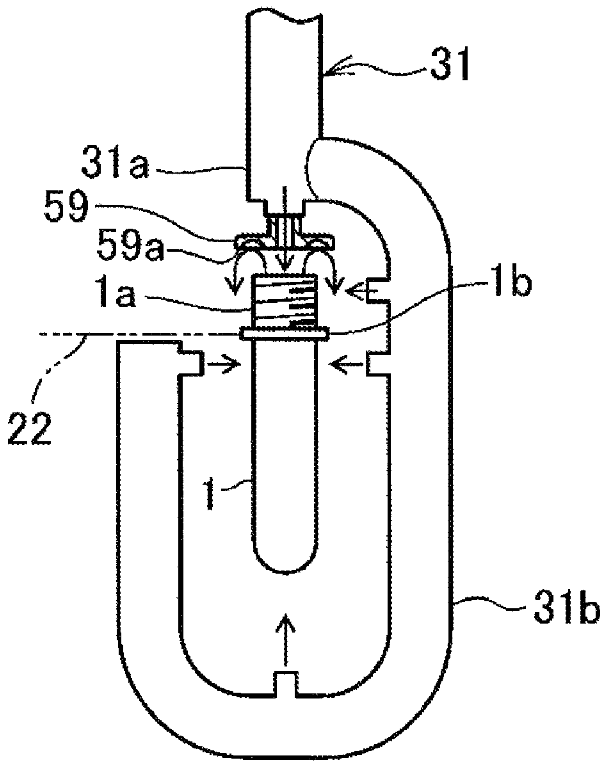

Sterilizing of the preform 1 that is illustrated in FIG. 10A can also be performed at a wheel 7 illustrated in FIG. 1. As illustrated in FIG. 10A, gas of the sterilizer is sprayed at the preform 1 from the sterilizer gas spraying nozzle 31. A sterilizer gas generator that is of the same kind as the sterilizer gas generator 51 which is used for sterilization of the bottle 2 is used for generating gas of the sterilizer. Further, a similar sterilizer is also used, and preferably the sterilizer contains at least hydrogen peroxide, and an appropriate range of the content thereof is from 0.5% by mass to 65% by mass. If the content is lower than 0.5% by mass, the sterilizing power may be insufficient in some cases, while if the content is higher than 65% by mass, the sterilizer will be difficult to handle from the viewpoint of safety. A further preferable range is from 0.5% by mass to 40% by mass. When the content is equal to or lower than 40% by mass, it is easier to handle the sterilizer.

Although the spray amount of the gas of the sterilizer can be arbitrarily set, when a hydrogen peroxide solution is adopted as the sterilizer the amount of hydrogen peroxide adhering to the preform 1 is preferably within the range of 0.001 $\mu L/cm^2$ to 0.5 $\mu L/cm^2$ as the amount of a hydrogen peroxide solution containing 35% by mass of hydrogen peroxide. If the adhering amount of hydrogen peroxide is less than 0.001 $\mu L/cm^2$, a sufficient sterilizing effect cannot be obtained. Further, if the adhering amount of hydrogen peroxide is more than 0.5 $\mu L/cm^2$, when the preform 1 is blow-molded to form the bottle 2, molding defects such as whitening, spots, wrinkles or deformation of the bottle will occur, and the residual amount of hydrogen peroxide in the bottle 2 will increase.

The gas of the sterilizer is sprayed from the sterilizer gas spraying nozzle 31 toward the preform 1, and as illustrated in FIG. 10A, the gas of the sterilizer may be divided into two streams to flow inside the sterilizer gas spraying nozzle 31, with one of the streams being sprayed toward the inside of the preform 1 from a nozzle 31*a*, and the other stream being sprayed toward the outer surface of the preform 1 from a spray-out hole provided in a nozzle 31*b*. After exiting from the sterilizer gas spraying nozzle 31, the gas of the sterilizer flows into the interior of the preform 1 or is sprayed at the outer surface of the preform 1 as it is in a gas state or in the form of a mist that is the condensate of the gas, or a mixture of the gas and mist.

Note that, a configuration may be adopted to prevent condensation of the sterilizer in the nozzles 31*a* and 31*b* by supplying hot air that is aseptic air from a location partway along the sterilizer gas spraying nozzle 31 and the nozzles 31*a* and 31*b*, respectively.

Further, the area around the gas of the sterilizer that is sprayed toward the interior of the preform 1 is covered by an umbrella-shaped member 59. A configuration may be adopted so that the gas, mist or a mixture thereof of the sterilizer which flowed into the preform 1 overflows from the mouth portion 1*a* of the preform 1, and a flow of the gas or the like that overflowed from the mouth portion 1*a* collides against the umbrella-shaped member 59 and is guided by an annular groove 59*a* provided in the inner surface of the umbrella-shaped member 59 so as to change the flow in the direction toward the outer surface of the preform 1 so as to be sprayed against the outer surface of the preform 1.

Bacteria and the like adhering to the surfaces of the preform 1 are sterilized by gas, mist or a mixture thereof of the sterilizer being sprayed against the inner and outer surfaces of the preform 1 in this way.

Note that, the preform may be preheating by blowing hot air against the preform 1 or the like immediately before spraying the gas of the sterilizer at the preform 1 as illustrated in FIG. 10A. The sterilizing effect with respect to the preform 1 can be further enhanced by the preheating.

In addition, a configuration may be adopted in which a plurality of the sterilizer gas spraying nozzles 31, and not just one, are disposed along the travelling path of the preform 1, and gas of the sterilizer from these sterilizer gas spraying nozzles 31 is sprayed toward the preform 1.

Figure 10B:
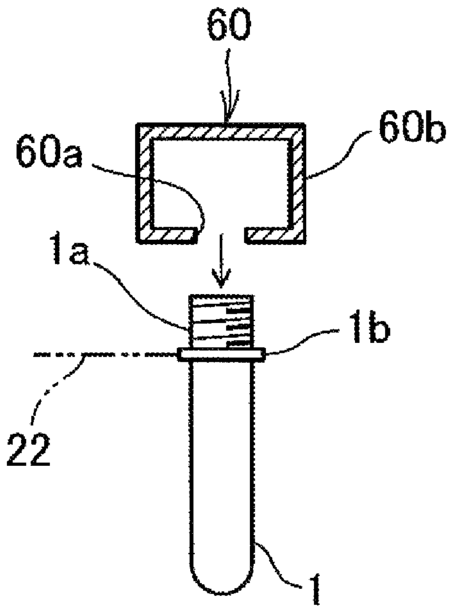

As illustrated in FIG. 10B, the preform 1 at which the gas of the sterilizer was sprayed may be gripped by the gripper 22, and aseptic air may be sprayed at the preform 1 by an air blowing nozzle 60 while the preform 1 is being conveyed. Depending on the kind and amount of sterilizer, blowing of aseptic air need not be performed.

By blowing aseptic air, sterilizer adhering to the surfaces of the preform 1 is activated, and bacteria and the like on the inner and outer surfaces of the preform 1 are sterilized. Furthermore, sterilizer adhering to the preform 1 is swiftly removed from the surfaces of the preform 1 by blowing the aseptic air. Sterilizer adhering to the preform 1 is removed from the preform 1 by blowing aseptic air prior to entering the heating furnace 12.

Although the aseptic air may be at ordinary temperature, by heating the aseptic air to produce aseptic hot air, the sterilizing effect increases, and in a case where the sterilizer contains hydrogen peroxide, the residual amount of hydrogen peroxide on the preform 1 also decreases. Heating of the aseptic air is preferably performed so that the temperature of the aseptic hot air that is blown at the preform 1 falls within the range of 40 to 140° C. If the temperature is lower than 40° C., the effect obtained by heating is small, and it is favorable if the temperature of the aseptic hot air does not exceed 140° C. because trouble such as deformation of the mouth portion 1*a* of the preform 1 will occur if the temperature of the preform 1 exceeds 70° C.

As illustrated in FIG. 10B, a configuration is adopted so that the air blows out from a slit-like blow-out hole 60*a* formed in a box-shaped manifold 60*b* that forms a principal part of the air blowing nozzle 60.

The spraying of gas of the sterilizer at the preform 1 illustrated in FIG. 10A and the blowing of aseptic air at the preform 1 illustrated in FIG. 10B are performed at the wheel 7 illustrated in FIG. 1, and a preform sterilization chamber 63 that covers the wheel 7 is exhausted to prevent the inflow of sterilizer into the molding portion 16. Exhaust air from the preform sterilization chamber 63 may be introduced into the exhaust gas mixing apparatus 57 that supplies air containing a sterilizer to the barrier chamber 49.

In the first embodiment of the present invention, sterilization may be performed with respect to the preform 1, may be performed with respect to the bottle 2, or may be performed with respect to both the preform 1 and the bottle 2. In a case where sterilization is only performed with respect to the preform 1, the atmosphere shut-off chamber 27, and the sterilizing portion 30 that performs bottle sterilization are unnecessary. The air-rinsing portion 34 also need not be provided.

Further, the discharging conveyor 62 may be provided in the wheel 46 illustrated in FIG. 1 of the first embodiment of the present invention. With regard to bottles which do not fall over on the aforementioned discharging conveyor, the bottles may be conveyed by the discharging conveyor 62 that is provided in a connected state to the wheel 46 and discharged to outside of the aseptic filling machine, without operating the barrier chamber 49 and the outlet chamber 61. In a case where the discharging conveyor 62 is not used, closing a shutter provided at the discharge end will ensure that the aseptic condition of the filling portion chamber 41 is not lost.

Second Embodiment

Firstly, an outline of an aseptic filling machine composed of a molding portion, a sterilizing portion, a filling portion, and a discharge portion will be described starting from the supply of a preform by way of FIG. 11, and the details of each portion will be described by way of FIG. 12, FIG. 13 and FIG. 14. The operations from a preform supplying step to a sealing step are the same as in the first embodiment. According to the second embodiment, even if a bottle falls over on a discharging conveyor in the aseptic zone due to the base of the bottle being a petaloid shape or the bottle having an unstable shape, the fallen bottle can be removed by simply releasing the aseptic condition within the discharge portion chamber. Since operation of the aseptic filling machine can be resumed thereafter by sterilizing only the inside of the discharge portion chamber, the stopping time of the aseptic filling machine can be shortened.

(Outline of Aseptic Filling Machine and Aseptic Filling Method)

Figure 11:
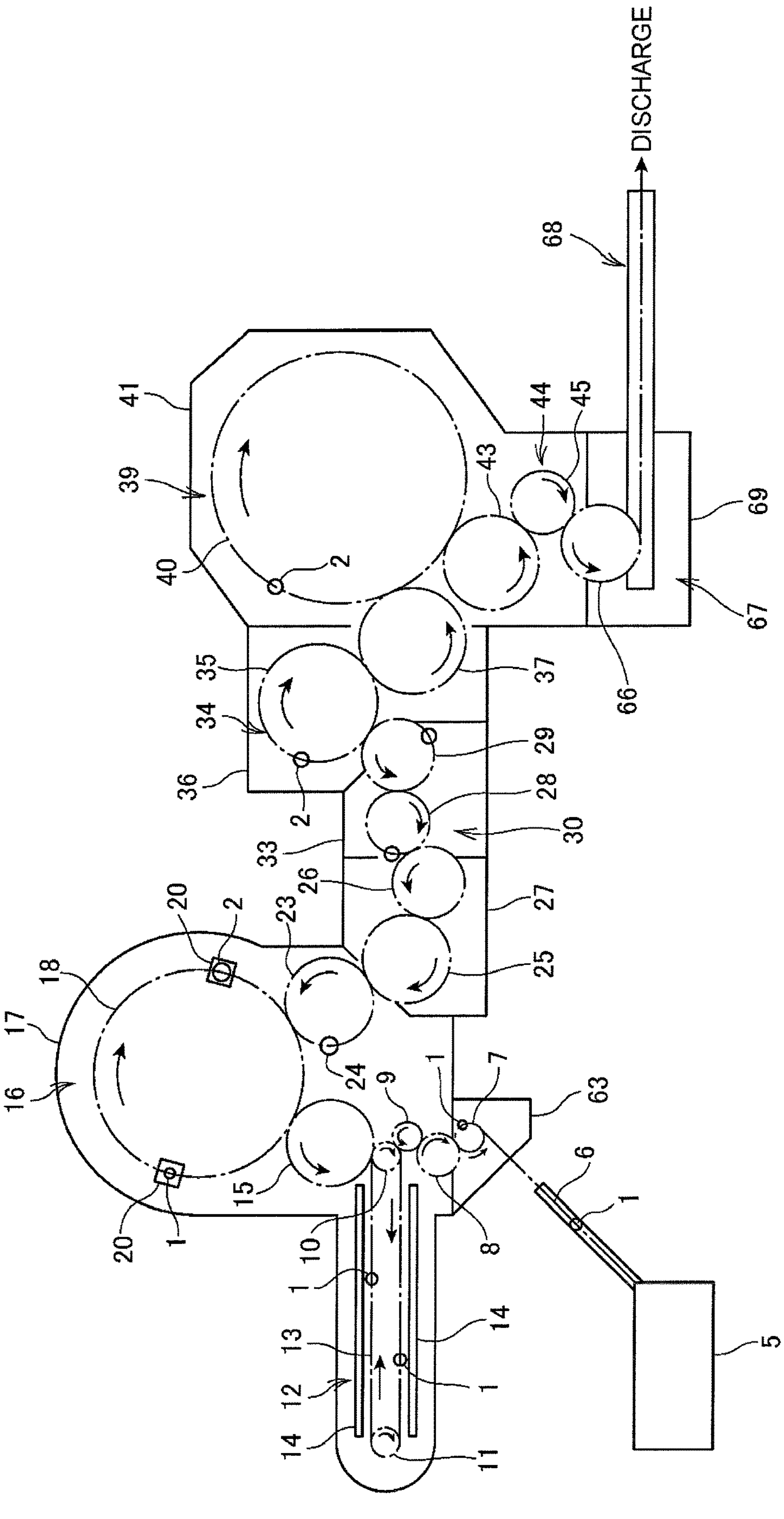
FIG. 11 is a plan view illustrating an outline of one example of an aseptic filling machine according to a second embodiment of the present invention.

As illustrated in FIG. 11, the aseptic filling machine according to the second embodiment includes: a preform supplying apparatus 5 that supplies a preform 1; a molding portion 16 that molds the preform 1 into a bottle 2; a sterilizing portion 30 that sterilizes the bottle 2 that was molded; an air-rinsing portion 34 that performs air-rinsing of the sterilized bottle 2; a filling portion 39 that fills sterilized content into the bottle 2 that was subjected to air-rinsing; and a sealing portion 44 that seals the bottle 2 with a sterilized cap 4. In addition, the aseptic filling machine includes a discharge portion 67 within which the sealed bottle 2 is placed on a discharging conveyor 68 and is discharged into a non-aseptic zone.

The molding portion 16 is shielded by a molding portion chamber 17, the sterilizing portion 30 is shielded by a sterilizing portion chamber 33, the air-rinsing portion 34 is shielded by an air-rinsing portion chamber 36, the filling portion 39 and the sealing portion 44 are shielded by a filling portion chamber 41, and the discharge portion 67 is shielded by a discharge portion chamber 69. An atmosphere shut-off chamber 27 is provided between the molding portion 16 and the sterilizing portion 30 to ensure that gas, mist or a mixture of gas and mist of a sterilizer that is generated at the sterilizing portion 30 does not flow into the molding portion 16. The inside of the atmosphere shut-off chamber 27 is exhausted, and therefore the gas, mist or mixture of gas and mist of a sterilizer generated at the sterilizing portion 30 does not flow into the molding portion 16.

Aseptic air that was sterilized by an aseptic filter is supplied to the sterilizing portion chamber 33, the air-rinsing portion chamber 36, the filling portion chamber 41, and the discharge portion chamber 69, and the interior of each of these chambers is maintained at a positive pressure. The pressure which is maintained at a positive pressure is set to be highest in the filling portion chamber 41, and to be progressively lower toward the upstream side, with the pressure being set lower in the air-rinsing portion chamber 36 than the filling portion chamber 41, and set further lower in the sterilizing portion chamber 33. The atmosphere shut-off chamber 27 is exhausted so that the inside thereof is maintained at approximately the same pressure as the atmospheric pressure. In addition, the pressure inside the discharge portion chamber 69 is set lower than the pressure inside the filling portion chamber 41.

(Detailed Description of Aseptic Filling Machine and Aseptic Filling Method)

First, the preforms 1 illustrated in FIG. 4A are conveyed from the preform supplying apparatus 5 illustrated in FIG. 11 to the molding portion 16 consecutively at a desired speed by a preform conveyance conveyor 6.

The preform 1 in the second embodiment is the same as in the first embodiment. The preform 1 that is supplied to the molding portion 16 is heated to a temperature that is suitable for subsequent blow molding, in a heating furnace 12 similarly to the first embodiment. The heated preform 1 is released from a spindle 19 and is gripped by a gripper 22, and is conveyed to a mold wheel 18 of a blow molding machine via a wheel 15. The preform 1 is blow-molded into the form of a bottle 2 at the mold wheel 18, similarly to the first embodiment. A bottle 2 that is molded is taken out from a mold 20, and transferred to an inspection wheel 23.

The bottle 2 that is molded by the aseptic filling machine according to the second embodiment of the present invention has a petaloid-shaped base as illustrated in FIG. 2. When a carbonated drink is filled in a bottle such as a bottle 3 having a substantially flat base as illustrated in FIG. 3, the base may sometimes bulge in a convex shape due to an increase in the internal pressure directly after filling. Therefore, when filling a carbonated drink, the bottle 2 having a petaloid shape that has petaloid legs 2*a* at the base thereof as illustrated in FIG. 2 is used. The number of petaloid legs 2*a* is usually set arbitrarily within the range of 5 to 9. The depth of a valley portion of each petaloid leg 2*a* is also arbitrarily set. A bottle that is molded by the aseptic filling machine according to the embodiment of the present invention may also have a shape like the commonly used bottle 3 that has a substantially flat base that is illustrated in FIG. 3. In particular, the aseptic filling machine according to the present invention is suitable for a bottle that is unstable even though the base thereof is flat.

The molded bottle 2 is subjected to an inspection in a similar manner to the first embodiment by an inspection machine 24 that is provided at the periphery of the inspection wheel 23, and if the molded bottle 2 is determined as being abnormal, the bottle 2 is discharged to outside of the aseptic filling machine by an unshown discharging apparatus.

The bottles 2 which are not determined as abnormal by the inspection by the inspection machine 24 are conveyed to the sterilizing portion 30 via wheels 25 and 26 inside the atmosphere shut-off chamber 27 that is provided between the molding portion 16 and the sterilizing portion 30 so as to ensure that gas, mist or a mixture of gas or mist of the sterilizer that arises at the sterilizing portion 30 does not flow into the molding portion 16.

The bottle 2 that is conveyed to the sterilizing portion 30 is sterilized in a similar manner to the first embodiment at a wheel 28. The bottle 2 that was sterilized at the sterilizing portion 30 is conveyed to the air-rinsing portion 34 via a wheel 29. At the air-rinsing portion 34, aseptic air is blown at the bottle 2 in a similar manner to the first embodiment. The bottle 2 that was rinsed with air at the air-rinsing portion 34 is conveyed to the filling portion 39 via a wheel 37. At the filling portion 39, content is filled into the bottle 2 by a filling nozzle 42 in a similar manner to the first embodiment. The bottle 2 into which content was filled is conveyed to the sealing portion 44 via a wheel 43. At a sealing wheel 45 provided in the sealing portion 44, a cap 4 that was sterilized in advance is screwed onto the mouth portion 1*a* of the bottle 2 in a similar manner to the first embodiment by a capper which is provided in the sealing wheel 45, to thereby seal the bottle 2.

The sealed bottle 2 is transferred from the gripper 22 of the sealing wheel 45 to the gripper 22 of a discharging wheel 66 of the discharge portion 67. The bottle 2 that was transferred to the discharging wheel 66 is placed on the discharging conveyor 68. The bottle 2 that was placed on the discharging conveyor 68 is discharged to outside of the aseptic filling machine from inside the discharge portion chamber 69.

The interior of the discharge portion chamber 69 that shields the discharge portion 67 is sterilized prior to operation of the aseptic filling machine. Therefore, as illustrated in FIG. 12, a discharge portion chamber sterilization apparatus 70 which includes a sterilizer spraying nozzle 71 and a water spraying nozzle 72 is provided in the discharge portion chamber 69.

A single-fluid spray of a twin-fluid spray in which a sterilizer and compressed air are mixed together and sprayed is used for the sterilizer spraying nozzle 71, and the sterilizer is sprayed so as to adhere to the entire area inside the discharge portion chamber 69. The interior of the discharge portion chamber 69 is sterilized by the sprayed sterilizer. The sterilizer spraying nozzle 71 is disposed so that the sterilizer adheres to the entire area inside the discharge portion chamber 69. A sterilizer that is similar to the sterilizer used to sterilize the bottle 2 can be used for sterilizing the inside of the discharge portion chamber 69, and use of a sterilizer containing peracetic acid or hydrogen peroxide is preferable. Spraying of the sterilizer may be performed by spraying multiple time using different kinds of sterilizer.

After sterilizer is sprayed from the sterilizer spraying nozzle 71, water is sprayed over the entire area of the discharge portion chamber 69 by the water spraying nozzle 72. Sterilizer that remains inside the discharge portion chamber 69 is cleaned away by the water. The water spraying nozzle 72 is disposed so that the water is sprayed over the entire area inside the discharge portion chamber 69. Water that is sterilized by being heated to 121° C. or higher for 4 minutes or more or by being passed through an aseptic filter is used. Preferably, the water that is sprayed into the discharge portion chamber 69 from the water spraying nozzle 72 is heated to within a range of 60 to 100° C. For example, a spray nozzle that uses a spin ball is used as the water spraying nozzle 72. A configuration may also be adopted in which the water spraying nozzle 72 is not provided, and water is sprayed from the sterilizer spraying nozzle 71.

Figure 12:
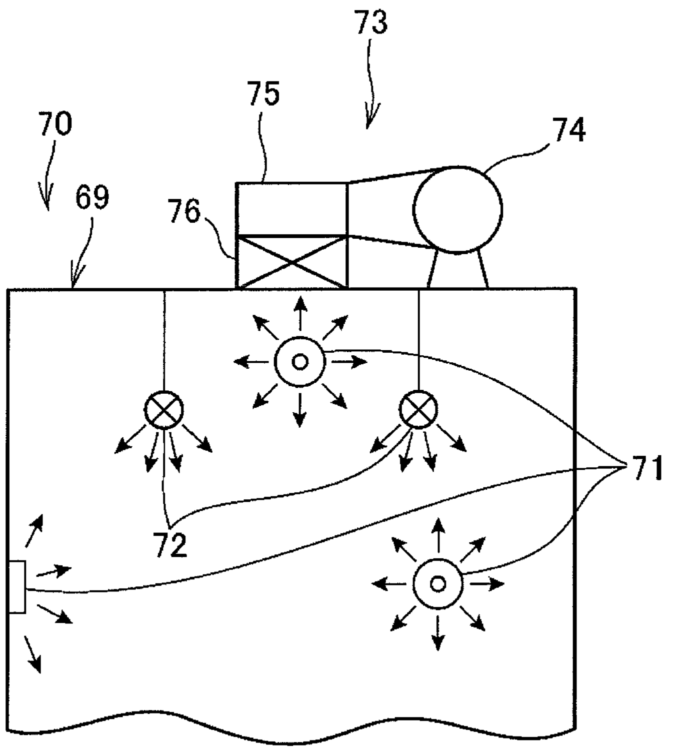
FIG. 12 is a view illustrating a discharge portion chamber sterilization apparatus that is incorporated into the aseptic filling machine according to the second embodiment of the present invention.

As illustrated in FIG. 12, an aseptic air supplying apparatus 73 is also provided in the discharge portion chamber 69. The aseptic air supplying apparatus 73 is connected to an upper portion of the discharge portion chamber 69. The aseptic air supplying apparatus 73 includes a blower 74, a heating apparatus 75 and an aseptic filter 76. Air from the blower 74 is heated by the heating apparatus 75, and the heated air is sterilized by the aseptic filter 76, and thereafter is supplied as aseptic air into the discharge portion chamber 69.

Water that was sprayed from the water spraying nozzle 72 and remains in the discharge portion chamber 69 is vaporized and removed by the aseptic air (at ordinary temperature or heated) that is supplied from the aseptic air supplying apparatus 73. At this time, by heating the aseptic air, removal of the water by vaporization is swiftly performed. Further, the aseptic air supplying apparatus 73 supplies aseptic air into the discharge portion chamber 69 in order to maintain the aseptic condition inside the discharge portion chamber 69 during operation of the aseptic filling machine. In this case, it is not necessary for the aseptic air to be heated.

Prior to spraying the sterilizer into the discharge portion chamber 69, the interior of the discharge portion chamber may be cleaned by spraying an aqueous solution of an alkaline compound such as sodium hydroxide or potassium hydroxide. Further, after spraying the sterilizer, aseptic hot air may be blown without performing water spraying.

The inside of the discharge portion chamber 69 is kept at a positive pressure by the supply of aseptic air, and aseptic air that flows out from the discharge portion chamber 69 is streamed from an opening for discharging bottles. A configuration may also be adopted in which an exhaust apparatus is provided in the discharge portion chamber 69. Although the inside of the discharge portion chamber 69 is kept at a positive pressure, the pressure in the discharge portion chamber 69 is set to a lower pressure than in the filling portion chamber 41 which is kept at a positive pressure by aseptic air. For example, in a case where the internal pressure of the filling portion chamber 41 is in the range of 20 Pa to 40 Pa, the internal pressure of the discharge portion chamber 69 is set, for example, within the range of 10 Pa to 30 Pa, which is a lower pressure than inside the filling portion chamber. Further, because the pressure inside the discharge portion chamber 69 increases when performing sterilization and cleaning of the interior of the discharge portion chamber 69, the pressure inside the filling portion chamber 41 is set to 50 Pa or higher, and preferably 100 Pa or higher.

When performing sterilization prior to operation of the aseptic filling machine, the surface of the aseptic filter 76 can also be sterilized by spraying the sterilizer by means of the sterilizer spraying nozzle 71. Sterilization of the surface of the aseptic filter 76 is preferably performed by sterilizing using a gas, a mist or a mixture of gas and mist of a hydrogen peroxide solution.

The order as well as the number of times for performing spraying of a sterilizer, spraying of water and supply of aseptic air can be arbitrarily set, and any order and number of times may be adopted as long as the conditions adopted are such that the interior of the discharge portion chamber 69 is sterilized.

Figure 13:
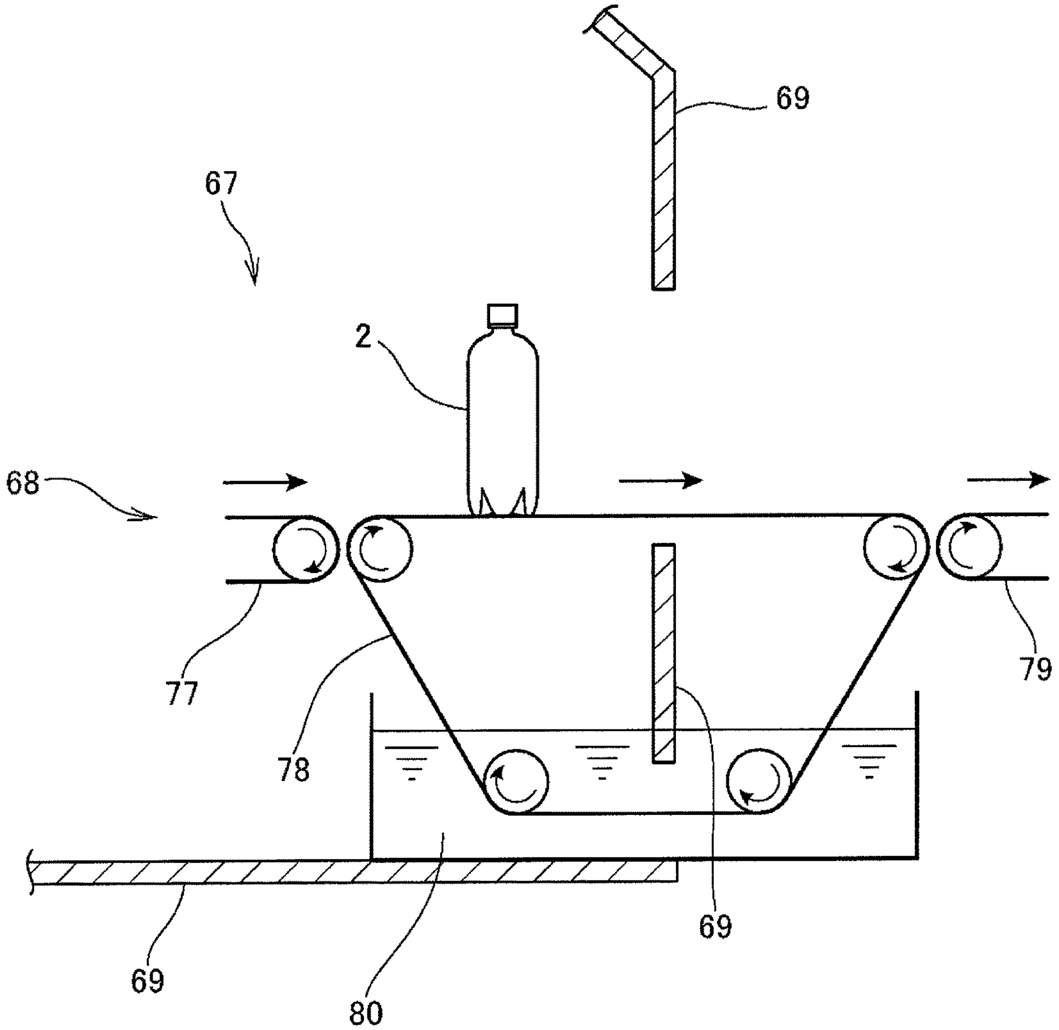
FIG. 13 is a side view illustrating a discharging conveyor that is incorporated into the aseptic filling machine according to the second embodiment of the present invention.

As illustrated in FIG. 13, the bottle 2 is conveyed to a non-aseptic zone by the discharging conveyor 68 from the discharge portion 67 in which an aseptic atmosphere is maintained. The discharging conveyor 68 includes a first conveyor 77, an intermediate conveyor 78 and a second conveyor 79. The intermediate conveyor 78 circulates between the aseptic zone and the non-aseptic zone. The intermediate conveyor 78 that enters into the non-aseptic zone is immersed in sterilizer in a sterilizer tank 80 and thereby sterilized, and then returns to the aseptic zone. Even if the intermediate conveyor 78 is contaminated by bacteria and the like in the non-aseptic zone, because the intermediate conveyor 78 is sterilized by being immersed in the sterilizer tank 80, the contamination is not brought into the aseptic zone.

As illustrated in FIG. 13, the discharge portion chamber 69 is opened at a place at which the bottle 2 is discharged. In order to minimize the area of the opening portion, the lower portion of the intermediate conveyor 78 may be shielded and the shielding plate may be suspended so that a part thereof is submerged in the sterilizer in the sterilizer tank 80.

The sterilizer that is supplied to the sterilizer tank 80 may be of any kind as long as the sterilizer is a liquid that contains a compound such as peracetic acid, hydrogen peroxide, or sodium hypochlorite and that is capable of sterilization.

Figure 14:
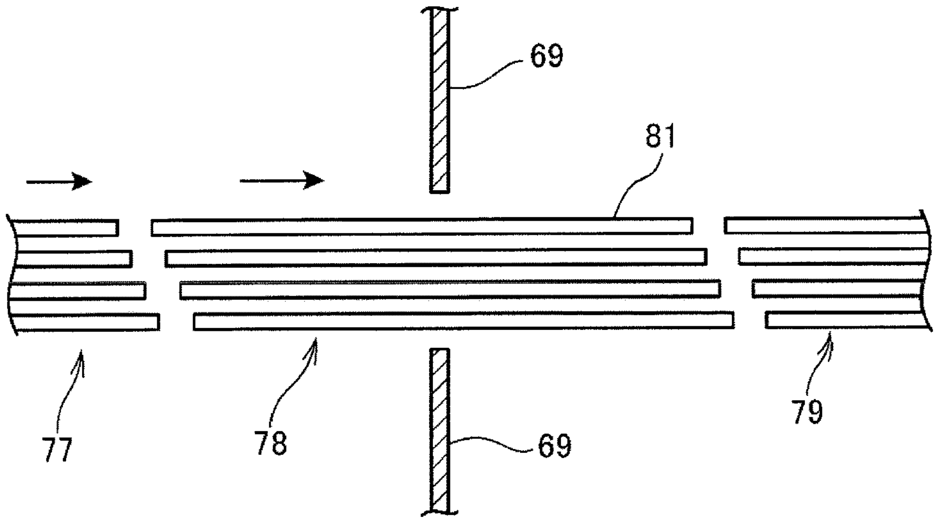
FIG. 14 is a plan view illustrating the discharging conveyor that is incorporated into the aseptic filling machine according to the second embodiment of the present invention.

As illustrated in FIG. 14, the first conveyor 77, the intermediate conveyor 78 and the second conveyor 79 are composed of a plurality of thin conveyor chains 81, and all the conveyor chains 81 move at the same speed. At the connecting portions between the first conveyor 77 and intermediate conveyor 78, and the intermediate conveyor 78 and second conveyor 79, the respective conveyor chains 81 are joined diagonally from the ends. By means of such joints, the bottle 2 is conveyed between the conveyors without hindrance. However, if a petaloid leg 2*a* enters into a gap in the joints, the bottle 2 may fall over.

In a case where the bottle 2 falls over between the first conveyor 77 and the intermediate conveyor 78, it is necessary to open up the discharge portion chamber 69 and remove the bottle 2 that fell over. Conventionally it is necessary to open up the filling portion chamber 41 that has a large capacity and includes a large number of apparatuses. However, according to the present embodiment, operation of the aseptic filling machine can be resumed by sterilizing only the discharge portion chamber 69 in which there are a small number of apparatuses and in which the capacity is also small. Hence, the stopping time of the aseptic filling machine can be shortened.

The second embodiment of the present invention has been described in detail based on FIG. 11. The second embodiment described above is an aseptic filling machine that sterilizes the bottle 2 which is obtained by molding the preform 1. However, the present invention may be an aseptic filling machine that sterilizes the preform 1. Hereunder, as another embodiment, an aseptic filling machine that includes a sterilizing portion that sterilizes the preform 1 is described.

Similarly to the first embodiment, sterilization of the preform 1 can be performed at a wheel 7 illustrated in FIG. 11. The preform 1 at which gas of a sterilizer is sprayed may be subjected to spraying with aseptic air in a similar manner to the first embodiment. In the second embodiment of the present invention, sterilization may be performed with respect to the preform 1, may be performed with respect to the bottle 2, or may be performed with respect to both the preform 1 and the bottle 2. In the case of sterilizing only the preform 1, the atmosphere shut-off chamber 27 and the sterilizing portion 30 which performs bottle sterilization are not required. Further, the air-rinsing portion 34 need not be provided.

The present invention is configured as described above. However, the present invention is not limited to the embodiments described above, and various modifications can be made without departing from the spirit of the present invention.

REFERENCE SIGNS LIST

1 preform
2 bottle
12 heating furnace
16 molding portion
20 mold
22 gripper
24 inspection machine
30 sterilizing portion
31 sterilizer gas spraying nozzle
34 rinsing portion
39 filling portion
44 sealing portion
49 barrier chamber
50 apparatus for supplying sterilizer-containing air
51 sterilizer gas generator
57 exhaust gas mixing apparatus
62 discharging conveyor
64 label attaching apparatus
67 discharge portion
68 discharging conveyor
69 discharge portion chamber
70 discharge portion chamber sterilization apparatus
73 aseptic air supplying apparatus

The invention claimed is:

1. An aseptic filling machine for bottles that comprises at least a sterilizing portion, a filling portion and a sealing portion, wherein a barrier chamber including a supply apparatus for air containing a sterilizer is provided downstream of the sealing portion, the barrier chamber has an inside and the supply apparatus supplies the air containing the sterilizer to the inside of the barrier chamber when a sealed bottle is conveyed into the barrier chamber.

2. The aseptic filling machine according to claim 1, wherein an outlet chamber comprising an exhaust apparatus is provided downstream of the barrier chamber.

3. The aseptic filling machine according to claim 2, wherein a conveying apparatus is provided which conveys the bottle from the sealing portion to the barrier chamber and the outlet chamber and also grips or supports a mouth portion of the bottle to convey the bottle.

4. The aseptic filling machine according to claim 2, wherein a conveyor is provided which conveys the bottle that is inside the outlet chamber to outside of the aseptic filling machine.

5. The aseptic filling machine according to claim 2, wherein a label attaching apparatus is provided which attaches a label to the bottle inside the outlet chamber.

6. The aseptic filling machine according to claim 1, wherein the sterilizer contains hydrogen peroxide.

7. The aseptic filling machine according to claim 1, wherein an exhaust gas blower is provided for exhausting air from the sterilizing portion, and an exhaust air mixing apparatus is provided for mixing air that is exhausted from the sterilizing portion with the air containing a sterilizer.

8. An aseptic filling method comprising at least a sterilization step of sterilizing a preform or a bottle, a filling step of filling sterilized content into the bottle in an aseptic atmosphere, and a sealing step of sealing the bottle in which the content is filled with a sterilized cap in an aseptic atmosphere, wherein, after the sealing step, the bottle that is sealed is conveyed into a barrier chamber having an inside and air containing a sterilizer is supplied into the inside of the barrier chamber.

9. The aseptic filling method according to claim 8, wherein the bottle that is conveyed to the barrier chamber is conveyed to an outlet chamber that comprises an exhaust apparatus.

10. The aseptic filling method according to claim 9, wherein a mouth portion of the bottle is gripped or supported, and the bottle is conveyed to the barrier chamber and the outlet chamber.

11. The aseptic filling method according to claim 9, wherein the bottle is discharged to outside of an aseptic filling machine by a conveyor that is provided within the outlet chamber.

12. The aseptic filling method according to claim 9, wherein, after the bottle is conveyed to the outlet chamber, a label is attached to the bottle.

13. The aseptic filling method according to claim 8, wherein the sterilizer contains hydrogen peroxide.

14. The aseptic filling method according to claim 8, wherein air in the sterilization step is exhausted, and the air that is exhausted in the sterilization step is mixed with the air containing a sterilizer.

* * * * *